(12) United States Patent
Wu

(10) Patent No.: US 8,768,660 B2
(45) Date of Patent: Jul. 1, 2014

(54) NUMERICALLY SIMULATING STRUCTURAL BEHAVIORS OF EMBEDDED BI-MATERIALS USING MESHFREE METHOD

(75) Inventor: Cheng-Tang Wu, Livermore, CA (US)

(73) Assignee: Livermore Software Technology Corp., Livermore, CA (US)

( * ) Notice: Subject to any disclaimer, the term of this patent is extended or adjusted under 35 U.S.C. 154(b) by 470 days.

(21) Appl. No.: 13/251,654

(22) Filed: Oct. 3, 2011

(65) Prior Publication Data

US 2013/0085727 A1 Apr. 4, 2013

(51) Int. Cl.
*G06F 7/60* (2006.01)
*G06F 17/10* (2006.01)
*G06F 17/50* (2006.01)
*G06T 17/20* (2006.01)

(52) U.S. Cl.
CPC ............ *G06F 17/5018* (2013.01); *G06T 17/20* (2013.01); *G01N 2203/0216* (2013.01); *G06F 2217/16* (2013.01); *G06F 2217/44* (2013.01)
USPC ........... 703/2; 703/1; 703/6; 345/420; 700/98

(58) Field of Classification Search
CPC ............ G06F 17/5018; G06F 2217/16; G06F 2217/44; G06T 17/20; G01N 2203/0216
USPC ............................................................. 703/2
See application file for complete search history.

(56) References Cited

U.S. PATENT DOCUMENTS

| | | | |
|---|---|---|---|
| 6,718,291 B1 * | 4/2004 | Shapiro et al. .................... | 703/2 |
| 7,499,050 B2 * | 3/2009 | Wu et al. ........................ | 345/420 |
| 7,660,480 B1 * | 2/2010 | Wu et al. ........................ | 382/264 |
| 8,479,588 B1 * | 7/2013 | Simkins, Jr. .................... | 73/799 |

OTHER PUBLICATIONS

Sukumar et al, "Modeling Holes and Inclusions by Level Sets in the Extended Finite Element Method", Comput. Methods Appl. Mech. Engrg. 190, 2001.*
Belytschko et al, "A Coupled Finite Element-Element-Free Galerkin Method", Computational Mechanics 17, 1995.*
Krongauz et al, "EFG Approximation with Discontinuous Derivatives", International Journal for Numerical Methods in Engineering, vol. 21, 1998) teaches utilizing meshless methods in modeling bi-materials (Figure 7), Liu et al ("A Fast Boundary Element Method for the Analysis of Fiber-Reinforced Composites Based on a Rigid Inclusion Model", Journal o.*

(Continued)

*Primary Examiner* — Mary C Jacob
(74) *Attorney, Agent, or Firm* — Roger H. Chu

(57) ABSTRACT

Methods and systems for numerically simulating structural behaviors of embedded bi-materials are disclosed. At least first and second grid models are created independently for an embedded bi-material that contains an immersed material embedded entirely within a base material. First group of meshfree nodes represents the entire domain (i.e., base plus immersed materials). Second group of meshfree nodes represents the immersed or embedded material, which includes all interface nodes and nodes located within a space bordered by the material interface. Numerical structural behaviors of the embedded bi-material are simulated using the first and second set of meshfree nodes with a meshfree method that combines two meshfree approximations. The first meshfree approximation covers the first set of meshfree nodes and is based on properties of the base material, while the second meshfree approximation covers the second set of meshfree nodes and is based on a differential between the immersed and base materials.

20 Claims, 9 Drawing Sheets

(56) References Cited

OTHER PUBLICATIONS

Karutz et al, "Automatic Adaptive Generation of a Coupled Finite Element/Element-Free Galerkin Discretization", Finite Elements in Analysis and Design, 38, pp. 1075-1091, 2002.*

Zhu et al, "Three-Dimensional Numerical Modelling by XFEM of Spring-Layer Imperfect Curved Interfaces with Applications to Linearly Elastic Composite Materials", International Journal for Numerical Methods in Engineering, Mar. 17, 2011.*

Hegen, D., "Element-Free Galerkin Methods in Combination with Finite Element Approaches", Comput. Methods Appl. Mech. Engrg. 135, 1996.*

Hu et al, "Locally Enhanced Voronoi Cell Finite Element Model (LE-VCFEM) for Simulating Involving Fracture in Ductile Microstructures Containing Inclusions", International Journal for Numerical Methods in Engineering, 76, 2008.*

Liu et al, "A Fast Boundary Element Method for the Analysis of Fiber-Reinforced Composites Based on a Rigid Inclusion Model", Journal of Applied Mechanics, vol. 72, Jan. 2005.*

* cited by examiner excellent# NUMERICALLY SIMULATING STRUCTURAL BEHAVIORS OF EMBEDDED BI-MATERIALS USING MESHFREE METHOD

BACKGROUND OF THE INVENTION

1. Field of the Invention

The present invention generally relates to methods, systems and software product used in the area of computer-aided engineering analysis (e.g., finite element method (FEM), meshfree method, etc.), more particularly to methods and systems for numerically simulation structural behaviors of embedded bi-materials (e.g., particle-reinforced composites, fiber-reinforced composites, etc.).

2. Description of the Related Art

A composite material is a microscopic or macroscopic combination of two or more distinct materials with a recognizable interface between them. Composite materials are developed because no single, homogeneous structural material could be found that had all of the desired characteristics for a given application. For example, fiber-reinforced composites are developed to replace aluminum alloys to provide high strength and fairly high stiffness at low weight without corrosion and fatigue.

For predicting the structural behaviors of such composite materials, computer aided engineering analysis has been used. However, numerically simulating embedded bi-materials using prior art approaches have a number of shortcomings.

A simplified embedded bi-material model in two-dimension and a corresponding prior art FEM model 120 are shown in FIG. 1. The bi-material 100 contains two materials: outer (base) material 102 and inner (embedded or immersed) material 104. The conventional FEM for numerically simulating such material requires a matching or conforming mesh across the material interface 110. Standard finite element shape functions are used to approximate the solution of the underlying boundary value problems. However, generating matching meshes (e.g., FEM mesh 120) suitable for the FEM is difficult in particular having interfaces in irregular geometries. Most of time, construction of matching meshes in interface problem requires substantial user interaction and is time-consuming. One example of the difficulty is shown as irregular grids in a region 122 surrounding the inner material.

Other prior art approaches have problems also. In one example, motar FEM uses a domain decomposition technique to treat mismatching meshes. However, motar FEM requires using Lagrange multipliers that sometimes violate the so-called "inf-sup" condition, which can lead to numerical instability (i.e., no solution). In another examples, "generalized FEM (GFEM)", "the extended FEM (XFEM)", "immersed FEM (IFEM)" have been used but the results are too expensive to achieve (e.g., very high computational requirements/costs or not clear to apply in three-dimension).

Another prior art approach is based on meshfree method. Meshfree method has become one of the focused research topics during the 1990's. Many applications of using meshfree analysis have been achieved in the past decade.

An exemplary mesh-free model 200 is shown in FIG. 2. A physical domain Ω 202 and its boundary or border Γ 203 are depicted. To represent the physical domain 202, a plurality of meshfree nodes 204 are used. The meshfree nodes representing the physical domain do not have a particular pattern. They may be regularly spaced or in arbitrary locations within the domain 202. These meshfree nodes may be located in the interior or on the boundary of the physical domain. Each of the nodes 204 contains a domain of influence or support 206-208. Terms "domain of influence" and "support" are used interchangeably hereinafter. The size and shape of the support for each node are arbitrary. For example, the shape of the support can be quadrilateral 206 or circular 208. In the case of three-dimensional support, the shape of the support may be spherical. The size of the support can be a one square foot or a 16-in radius circle support. The support can have irregular geometric shape.

Due to the flexibility of the meshfree nodal representation 204 of the physical domain 202, a practical way to create a computer model for the meshfree method is to use the FEM model's nodal data that is readily generated from a pre-processing software package. The pre-processing software may be a stand-alone software package or a built-in portion of an engineering design or analysis computer program product package.

However, for simulating structural behaviors of an embedded bi-material, prior art meshfree methods require adding interface constraints and a set of interface nodes to ensure the visibility of the interface in the numerical simulation results. Adding the interface nodes must be done manually. Further, each added node's integration cell must also be adjusted such that the domain integration can be properly conducted. Extending the manual nodal adjustment in the three-dimensional cases, it is not only nontrivial but sometimes impossible.

It would, therefore, be desirable to have a new improved computer aided engineering analysis method and system for numerically simulation structural behaviors of embedded bi-materials.

SUMMARY OF THE INVENTION

This section is for the purpose of summarizing some aspects of the present invention and to briefly introduce some preferred embodiments. Simplifications or omissions in this section as well as in the abstract and the title herein may be made to avoid obscuring the purpose of the section. Such simplifications or omissions are not intended to limit the scope of the present invention.

The present invention discloses methods and systems for numerically simulating structural behaviors of embedded bi-materials (e.g., composites). According to one aspect of the present invention, at least first and second grid models are created independently for an embedded bi-material that contains an immersed material (i.e., second material) embedded entirely within a base material (i.e., first material).

The first and second grid models are used for defining the geometry of the domain (i.e., embedded bi-material) and used as integration cell for meshfree method. The first grid model represents the base and immersed materials. The second grid model represents the immersed material.

A set of interface nodes is determined to define the material interface between the base and immersed materials. By examining the second grid model, those nodes of the second grid model located on the outer border or edge are designated as the interfaced nodes.

First and second groups of meshfree nodes are created basing on the grid models. The first group of meshfree nodes represents the entire domain (i.e., base plus immersed materials). The second group of meshfree nodes represents the immersed or embedded material, which includes all interface nodes and nodes located within a space bordered by the material interface.

Numerical structural behaviors of the embedded bi-material are simulated using the first and second set of meshfree nodes with a meshfree method that combines two meshfree approximations. The first meshfree approximation covers the first set of meshfree nodes and is based on properties of the base material, while the second meshfree approximation covers the second set of meshfree nodes and is based on a differential between the immersed and base materials.

Other objects, features, and advantages of the present invention will become apparent upon examining the following detailed description of an embodiment thereof, taken in conjunction with the attached drawings.

BRIEF DESCRIPTION OF THE DRAWINGS

These and other features, aspects, and advantages of the present invention will be better understood with regard to the following description, appended claims, and accompanying drawings as follows:

FIG. 4-1 is a schematic diagram showing an exemplary embedded bi-material in a two-dimension according to an embodiment of the present invention;

FIG. 4-2 is a diagram showing a grid model of the exemplary embedded bi-material of FIG. 4-1 in accordance with one embodiment of the present invention;

FIG. 4-3 is a diagram showing a first set of meshfree nodes and corresponding first background grid model of an exemplary embedded bi-material in accordance with one embodiment of the present invention;

FIG. 4-4 is a diagram showing a second set of meshfree nodes and corresponding second background grid model of an exemplary embedded bi-material in accordance with one embodiment of the present invention;

FIG. 4-5 is a chart showing nonconforming meshfree approximation near material interface of an exemplary embedded bi-material in accordance with one embodiment of the present invention;

FIG. 4-6 is a chart showing conforming meshfree approximation near material interface of an exemplary embedded bi-material in accordance with one embodiment of the present invention;

FIG. 4-7 and FIG. 4-8 are diagrams showing continuity along the material interface using nonconforming and conforming meshfree approximations in accordance with an embodiment of the present invention; and FIG. 5 is a function block diagram showing salient components of an exemplary computer system, in which one embodiment of the present invention may be implemented.

DETAILED DESCRIPTION OF THE INVENTION

In the following description, numerous specific details are set forth in order to provide a thorough understanding of the present invention. However, it will become obvious to those skilled in the art that the present invention may be practiced without these specific details. The descriptions and representations herein are the common means used by those experienced or skilled in the art to most effectively convey the substance of their work to others skilled in the art. In other instances, well-known methods, procedures, components, and circuitry have not been described in detail to avoid unnecessarily obscuring aspects of the present invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

Figure 3:
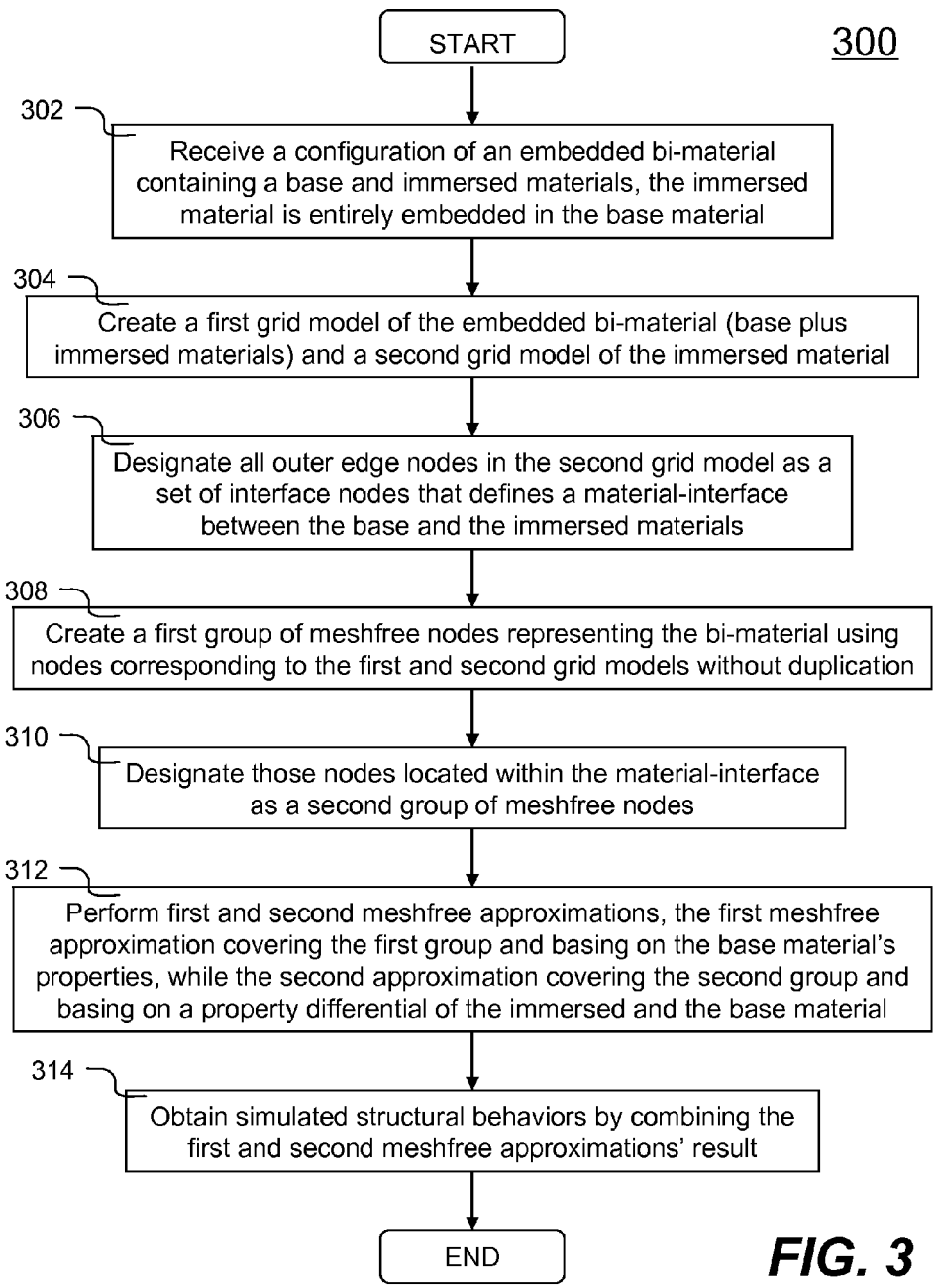
FIG. 3 is a flowchart illustrating an exemplary process of simulating structural behaviors of an embedded bi-material using meshfree method in accordance with one embodiment of the present invention.
Figures 1, 4:
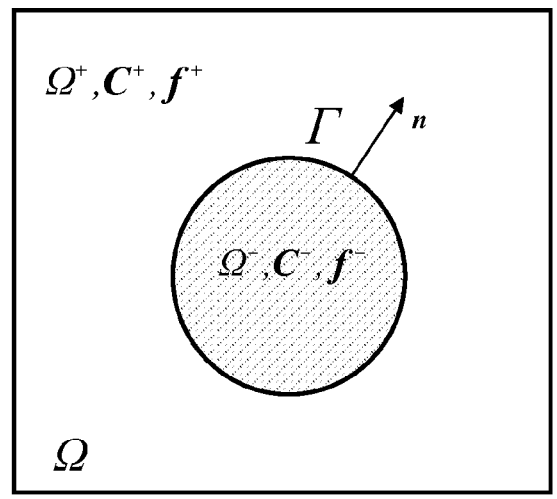
Figures 2, 4:
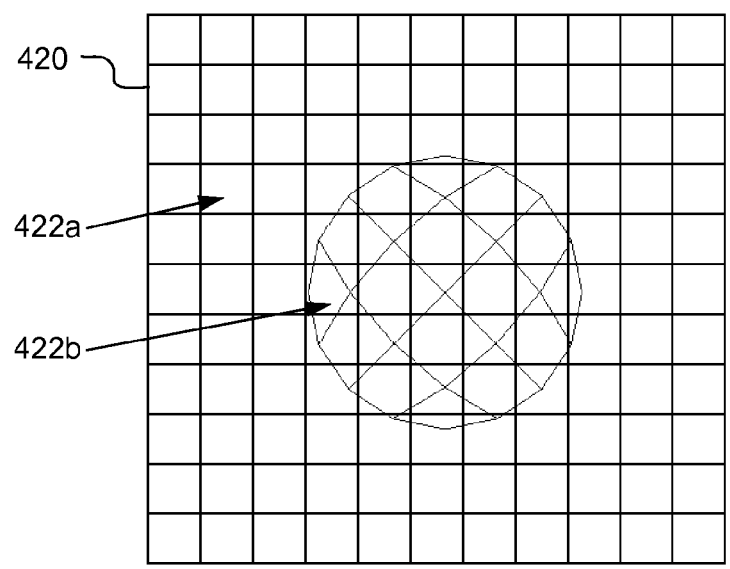
Figure 4:
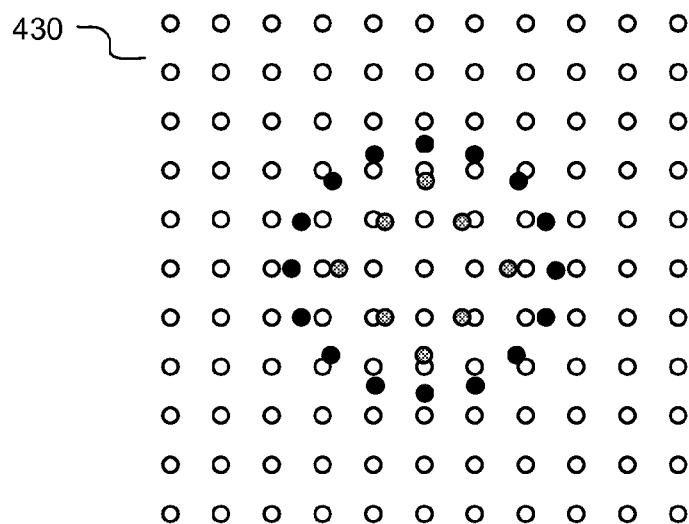
Figure 3:
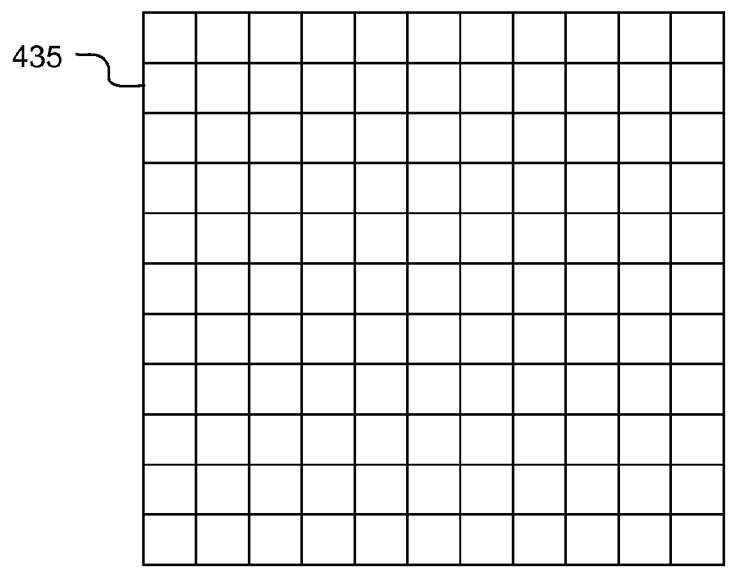
Figure 4:
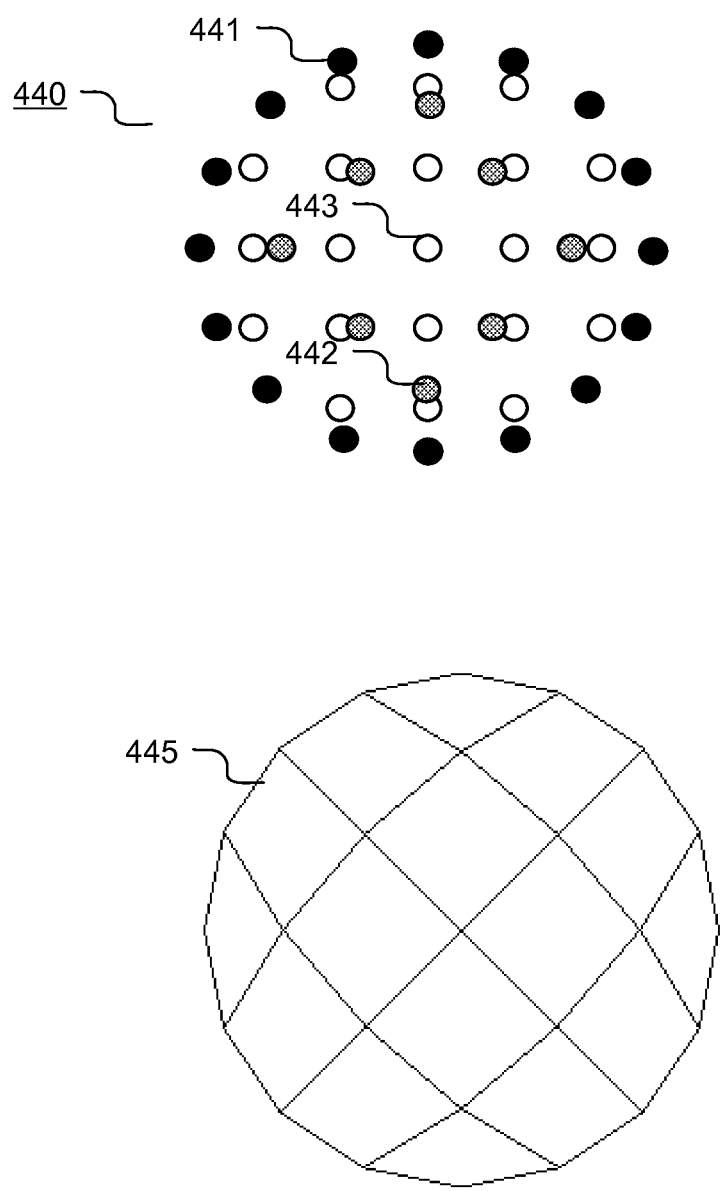
Figures 4, 5:
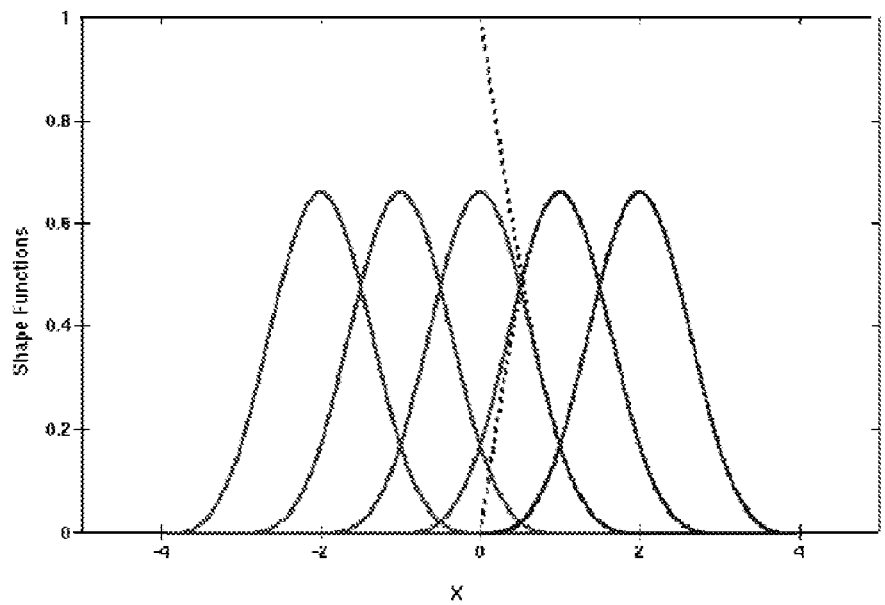

Embodiments of the present invention are discussed herein with reference to FIGS. 3-5. However, those skilled in the art will readily appreciate that the detailed description given herein with respect to these figures is for explanatory purposes as the invention extends beyond these limited embodiments.

Referring first to FIG. 3, it is shown a flowchart illustrating an exemplary process 300 of numerically simulating structural behaviors of an embedded bi-material in accordance with an embodiment of the present invention. Process 300 is preferably implemented in software and understood with other figures.

Process 300 starts by receiving configuration of an embedded bi-material at step 302. For example, the embedded bi-material contains base (outer) and immersed (inner) materials. The immersed material is entirely embedded inside the base material (i.e., see FIG. 4-1 as an example). Next, first and second computerized grid models (e.g., a finite element method mesh model) are created at step 304. The first computerized grid model represents the entire embedded bi-material (i.e., base plus immersed material), while the second computerized grid model represents the immersed material.

Figure 2:
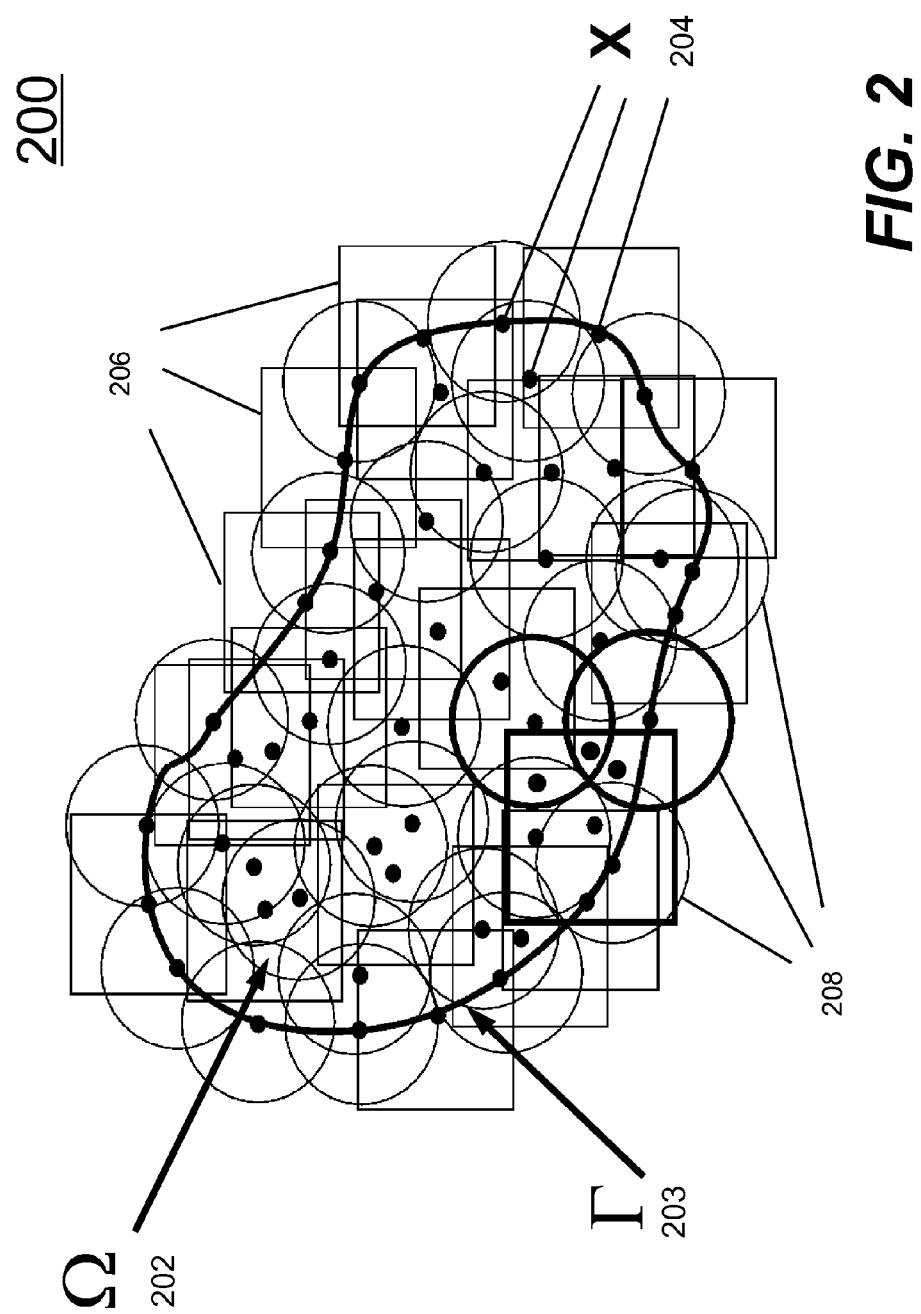
FIG. 2 is a schematic diagram showing an exemplary discretization of a domain using meshfree method.

Creations of the grid models are independent of each other. In other words, there is no correlation between these two grid models, for example, nodes need not to be matched or aligned. Each grid model contains a plurality of nodes that defines the mesh. FIG. 4-2 shows two exemplary grid models 422a-b overlapping each other.

Next, at step 306, a set of interface nodes is determined and designated. The set of interface nodes defines the material interface between the base and immersed materials. On exemplary method to determine the interface nodes is to examine the grid model of the immersed material (i.e., the second computerized grid model). Nodes located on the outer border/edge are designated as the interface nodes (shown as solid black circular dots 441 in FIG. 4-4).

At step 308, a first group of meshfree nodes representing the entire embedded bi-material is created. One exemplary method is to combine the nodes from the first and second grid models without any duplication. In other words, any duplicated node is removed during the combination procedure. An exemplary first group of meshfree nodes 430 (i.e., all circles—hollow, solid, filled) with a corresponding grid model 435 are shown in FIG. 4-3.

At step 310, a second group of meshfree nodes 440, shown in FIG. 4-4, is created by including the interface nodes 441 and those meshfree nodes 442-443 located within the interface nodes 441. Meshfree nodes 442 (shown as shaded circle) along with the interface nodes (shown as solid circular dots) are nodes created from the second grid model representing immersed material, while meshfree nodes 443 (shown as hollow circles) are those nodes created from the first grid model that are located within the material interface.

At step 312, at least two meshfree approximations (i.e., first and second meshfree approximations) are performed. The first meshfree approximation covers the first group of meshfree nodes and is carried out using the properties of the base material. The second meshfree approximation covers the second group of meshfree nodes and is carried out using a property differential between the immersed material and the base material. Two integrals of Eqs. (17)-(18) listed below represent these two meshfree approximations, respectively.

Finally, at step 314, numerically simulated structural behaviors (e.g., stresses, strains, displacements, etc.) are obtained by combing the first and the second meshfree approximations' result.

Problem Description and Variational Equation

Figure 1:
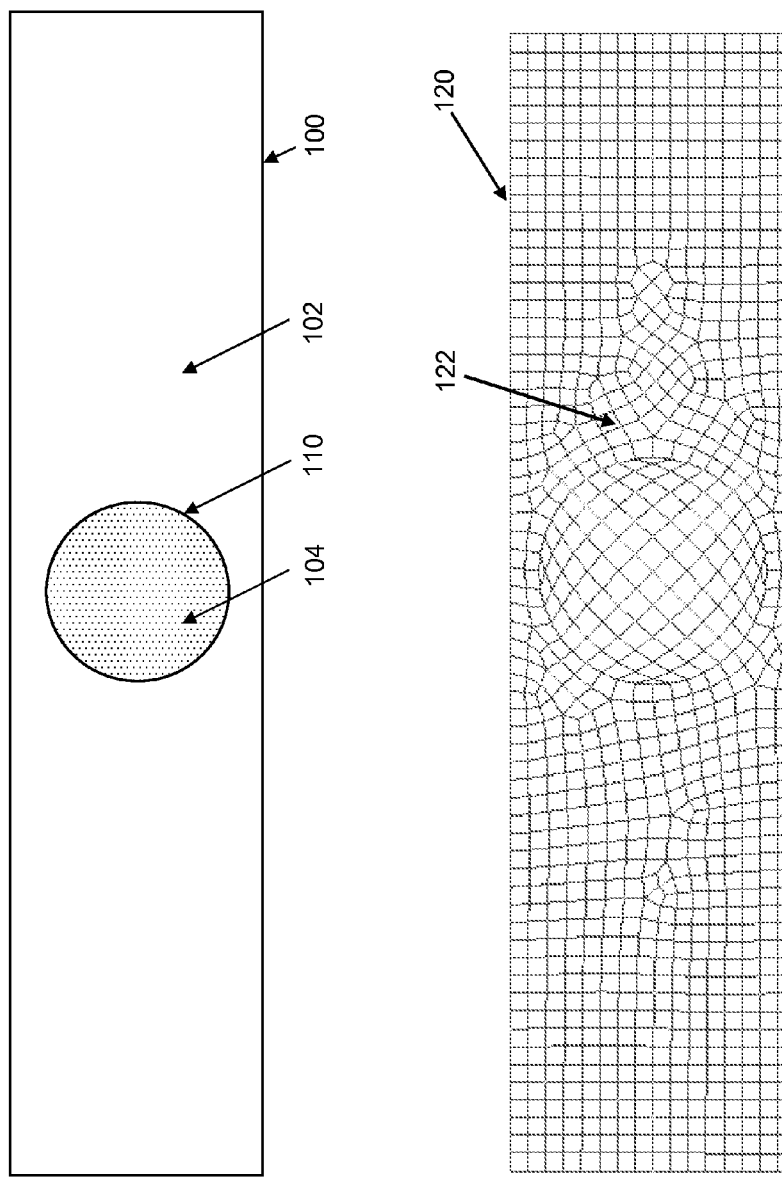
FIG. 1 is a schematic diagram showing a simplified two-dimensional embedded bi-material and a prior art finite element method model.

We consider an elastic solid occupying a bounded and open domain $\Omega \subset R^2$ with Lipschitz boundary. Let $\partial\Omega_D$ and $\partial\Omega_N$ be two open subsets of boundary $\partial\Omega$ such that $\partial\Omega=\partial\Omega_D\cup\partial\Omega_N$ and $\partial\Omega_D\cap\partial\Omega_N 0$. g(x) is the prescribed displacement applied on the Dirichlet boundary $\partial\Omega_D$, and $t(x)\epsilon L^2(\partial\Omega_N)$ is the prescribed traction applied on the Neumann boundary $\partial\Omega_N$ with $n_0$ denoting the outward unit normal to the boundary $\partial\Omega_N$. The elastic body is composed of two perfectly bounded material with zero-thickness interface $\Gamma$. The equilibrium configuration of the elastic body is characterized by the continuity of displacement and continuity of normal stress across the material interface $\Gamma$. The elasticity interface problem can be described by the following second-order elliptic boundary value problem with the associated homogenous Dirichlet and Neumann jump conditions on the interface $\Gamma$.

$$\begin{cases} -\nabla \cdot (C(x) \cdot \nabla_s u(x)) = f(x) & x \in \Omega \backslash \Gamma \\ u = g(x) & x \in \partial\Omega_D \\ C(x) \cdot \nabla_s u(x) \cdot n_0 = t(x) & x \in \partial\Omega_N \\ [\![u]\!] = 0 & x \in \Gamma \\ [\![C(x) \cdot \nabla_s u(x) \cdot n]\!] = 0 & x \in \Gamma \end{cases} \quad (1)$$

where function $u: \Omega \to R^2$ is the displacement and $f: \Omega \to R^2$ is the prescribed body force over the domain $\Omega$. Normally, $f \epsilon L^2(\Omega)$. The notation $\nabla_s u$ denotes the symmetric gradient of the displacement, $\nabla_s u=\frac{1}{2}(\nabla u+(\nabla u)^T)$. Without loss of generality, we assume the interface $\Gamma$ is a smoothed and closed curve that divides the global domain $\Omega$ into two regions: $\Omega^+$ representing the matrix and $\Omega^-$ denoting the immersed media or inclusion such that their union gives the global domain $\Omega$, $\overline{\Omega}=\overline{\Omega^+}\cup\overline{\Omega^-}$ and $\Gamma=\partial\Omega^+\cap\partial\Omega^-$ as depicted in FIG. 4-1. The symbol n denotes the outward unit normal vector on $\Gamma$. For simplicity, we further assume a convex domain $\Omega^- \subset R^2$ for inclusion. Correspondingly, we have a matrix domain $\Omega^+$ which is non-convex. We also define the jump operator $[\![\bullet]\!]$ by $$[\![q]\!](x)=q^+(x)-q^-(x) \quad (2)$$

in which + and − denote the two sides of the interface $\Gamma$ with the jump of quantity q across the interface. The body force and material constants can exhibit discontinuities across the interface $\Gamma$, but have smooth restrictions $f^+$, $C^+$ to $\Omega^+$ and $f^-$, $C^-$ to $\Omega^-$. They are given by $$f = \begin{cases} f^+ & \text{in } \Omega^+ \\ f^{-1} & \text{in } \Omega^- \end{cases} \quad (3)$$

and $$C = \begin{cases} C^+ & \text{in } \Omega^+ \\ C^- & \text{in } \Omega^- \end{cases}$$

The infinitesimal strain tensor $\epsilon(u)$ is defined by $$\epsilon(u)=\nabla_s u=\frac{1}{2}(\nabla u+(\nabla u)^T) \quad (4)$$

$C^+$ and $C^- \epsilon L^\infty(\Omega)$ are elasticity tensors with major and minor symmetries and are corresponding to different materials in $\Omega^+$ and $\Omega^-$ respectively. In the case of linear isotropic elasticity, we take $C^+$ and $C^-$ to be constants. The Cauchy stress tensor $\sigma$ and strain tensor $\epsilon$ have the following relationship $$\begin{cases} \sigma^+ = C^+ \cdot \varepsilon = 2\mu^+\varepsilon + \lambda^+ tr(\varepsilon)I & \text{in } \Omega^+ \\ \sigma^- = C^- \cdot \varepsilon = 2\mu^-\varepsilon + \lambda^- tr(\varepsilon)I & \text{in } \Omega^- \end{cases} \quad (5)$$

where the positive constants $\mu^+$, $\mu^-$ and $\lambda^+$, $\lambda^-$ are Lamé constants. The Lamé constants are related to the Young's modulus E and Poisson ratio v by $$\mu = \frac{E}{2(1+v)}, \quad (6)$$

$$\lambda = \frac{vE}{(1+v)(1-2v)}$$

The variational form of this problem is to find the displacement $u \epsilon V^g=\{v \epsilon H^1(\Omega): v=g \text{ on } \partial\Omega_D\}$ such that for all $v \epsilon V$ $$a(u,v)=l(v) \quad (7)$$

where the functional space $V=H_0^1(\Omega)$ consists of functions in Sobolev space $H^1(\Omega)$ which vanish on the boundary $\partial\Omega$ and is defined by $$V(\Omega)=\{v: v \epsilon H^1, v=0 \text{ on } \partial\Omega_D\} \quad (8)$$

The bilinear form $a(\bullet,\bullet)$ and linear functional $l(\bullet)$ are obtained by multiplying the test function $v \epsilon V$ to both sides of Eq. (7) and integrating over the regions $\Omega^+$ and $\Omega^-$ separately using Green's formula.

$$\int_{\Omega^+} f^+(x) \cdot v \, d\Omega + \int_{\Omega^-} f^-(x) \cdot v \, d\Omega = \quad (9)$$

$$-\int_{\Omega^+} \nabla \cdot (C^+(x) \cdot \nabla_s u(x)) \cdot v \, d\Omega - \int_{\Omega^-} \nabla \cdot (C^-(x) \cdot \nabla_s u(x)) \cdot v \, d\Omega =$$

$$\int_{\Omega^+} \varepsilon(u) \cdot C^+ \cdot \varepsilon(v) \, d\Omega -$$

$$\int_\Gamma C^+(x) \cdot \nabla_s u(x) \cdot n^+ \cdot v \, d\Gamma + \int_{\Omega^-} \varepsilon(u) \cdot C^- \cdot \varepsilon(v) \, d\Omega -$$

$$\int_\Gamma C^-(x) \cdot \nabla_s u(x) \cdot n^- \cdot v \, d\Gamma - \int_{\partial\Omega_N} (t \cdot v) \, d\partial\Omega$$

Using the fact that $n^+=-n^-$, we can rewrite the above equation to $$\int_{\Omega^+} f^+(x) \cdot v \, d\Omega + \int_{\Omega^-} f^-(x) \cdot v \, d\Omega = \quad (10)$$

$$\int_{\Omega^+} \varepsilon(u) \cdot C^+ \cdot \varepsilon(v) \, d\Omega + \int_{\Omega^-} \varepsilon(u) \cdot C^- \cdot \varepsilon(v) \, d\Omega -$$

$$\int_{\partial\Omega_N} (t \cdot v) \, d\partial\Omega - \int_\Gamma [\![C(x) \cdot \nabla_s u(x) \cdot n]\!] \cdot v \, d\Gamma$$

Applying the homogenous Neumann jump condition to Eq. (10) yields $$\int_{\Omega^+} \varepsilon(u) \cdot C^+ \cdot \varepsilon(v) d\Omega + \int_{\Omega^-} \varepsilon(u) \cdot C^- \cdot \varepsilon(v) d\Omega - \int_{\Omega^+} f^+ \cdot v d\Omega - \int_{\Omega^-} f^- \cdot v d\Omega - \int_{\partial \Omega_N} t \cdot v d\partial\Omega = a(u, v) - l(v) = 0 \quad (11)$$

where $$a(u, v) = \int_{\Omega^+} \varepsilon(u) \cdot C^+ \cdot \varepsilon(v) d\Omega + \int_{\Omega^-} \varepsilon(u) \cdot C^- \cdot \varepsilon(v) d\Omega \quad (12)$$

$$l(v) = \int_{\Omega^+} f^+ \cdot v d\Omega + \int_{\Omega^-} f^- \cdot v d\Omega + \int_{\partial \Omega_N} t \cdot v d\partial\Omega \quad (13)$$

It is noted that the elasticity tensors $C^+$ and $C^-$ are symmetric, and homogenous Neumann jump condition is enforced in the variational level. Obviously, the bilinear form $a(\cdot,\cdot)$ in Eq. (12) is symmetric, bounded and coercive by Friedrichs inequality. The existence and uniqueness of the problem is ensured by the Lax-Milgram theorem Embedded Meshfree Method for Interface Elasticity Problem This section first devotes to the development of a new meshfree discretization that spans across the material interface on the overlapping meshes. The definition of computation domain for the proposed method and the construction of the meshfree approximation that satisfies a point-wise continuity across the interface are described subsequently. Finally, a primal problem which is equivalent to a degenerated Lagrangain-type mortar method is devised and followed by a proof of the optimality.

Embedded Meshfree Discretization and Integration Cells

For simplicity, we assume that $\Omega$ is a convex polygonal domain and only consider the case of pure displacement problem under homogenous boundary condition ($\partial\Omega_D=0$). The standard meshfree Galerkin method is formulated on a finite dimensional space $V_h \subset V$ employing the variational formulation of Eq. (11) to find $u_h \in V_h$ such that $$a(u_h, v_h) = l(v_h) \forall v_h \in V_h \quad (14)$$

where $V_h = \text{span}\{\Psi_I: I \in Z_I\}$ and $Z_I$ is an index set. $\{\Psi_I(x)\}_{I \in Z_I}$ shape functions constructed using meshfree convex approximation and will be described later in this section. We also let $r_I \subset \Omega$ be the interior of the supp $\Psi_I(x)$. We assume that $r_I$ is star-shaped with respect to a ball $b_I \subset r_I$ and there exists a constant $C_r > 0$ such that $$\frac{\text{diam}(r_I)}{\text{diam}(b_I)} \geq C_r, \forall I \in Z_I \quad (15)$$

We let $h_I = \text{diam}(r_I)$ denote the nodal support radius and assume the following overlapping condition $$\exists M \in R \; \forall x \in \Omega \; \text{card} \; Z_I \leq M \quad (16)$$

Often, a shape function $\Psi_I(x)$ is associated with a particle $x_I \in R^2$ and particles are distinct. Using the superposition principle for the above linear system, the discrete bilinear form in Eq. (14) can be re-expressed by $$a(u_h, v_h) = \int_{\Omega^+} \varepsilon(u_h) \cdot C^+ \cdot \varepsilon(v_h) d\Omega + \int_{\Omega^-} \varepsilon(u_h) \cdot C^- \cdot \varepsilon(v_h) d\Omega \quad (17)$$

$$= \int_{\Omega^+ \cup \Omega^-} \varepsilon(u_h) \cdot C^+ \cdot \varepsilon(v_h) d\Omega + \int_{\Omega^-} \varepsilon(u_h) \cdot C^- \cdot \varepsilon(v_h) d\Omega -$$

$$\int_{\Omega^-} \varepsilon(u_h) \cdot C^+ \cdot \varepsilon(v_h) d\Omega$$

$$= \int_{\Omega^+ \cup \Omega^-} \varepsilon(u_h) \cdot C^+ \cdot \varepsilon(v_h) d\Omega +$$

$$\int_{\Omega^-} \varepsilon(u_h) \cdot (C^- - C^+) \cdot \varepsilon(v_h) d\Omega$$

Similarly, we have the discrete linear functional to be rewritten as $$l(v_h) = \int_{\Omega^+} f^+ \cdot v_h d\Omega + \int_{\Omega^-} f^- \cdot v_h d\Omega \quad (18)$$

$$= \int_{\Omega^+ \cup \Omega^-} f^+ \cdot v_h d\Omega + \int_{\Omega^-} f^- \cdot v_h d\Omega - \int_{\Omega^-} f^+ \cdot v_h d\Omega$$

$$= \int_{\Omega^+ \cup \Omega^-} f^+ \cdot v_h d\Omega + \int_{\Omega^-} (f^- - f^+) \cdot v_h d\Omega$$

The expression of discrete forms in Eqs. (17) and (18) allows us to reset the meshfree computation domain by two overlapping sub-regions; namely $\Omega^+ \cup \Omega^-$ and $\Omega^-$. The advantage of overlapping sub-regions is their flexibility to accommodate complex immersed structures in which different discretizations can be made easily and independently in each sub-region using finite element model. Since the computation domain $\Omega^-$ is "embedded" in computation domain $\Omega^+ \cup \Omega^-$ under the meshfree Galerkin framework, this method is referred to as an embedded meshfree method. FIG. 4-2 is an illustration of a domain 420 of overlapping sub-regions which shows a convex inclusion embedding in a base matrix using two overlapping finite element meshes 422a-b. It is evident that for the single-phase system ($C^+ = C^-$ and $f^+ = f^-$) the modified variational formulation can be degenerated to the standard meshfree Galerkin formulation.

Consequently, we can define the computational sub-regions as follows: Given a bounded domain $\Omega \subset R^2$, we consider sub-regions $\Omega_1$ and $\Omega_2$ to be the overlapping sub-regions satisfying $$\Omega = \bigcup_{i=1}^{2} \Omega_i \quad (19)$$

where $\Omega_1 = \Omega^+ \cup \Omega^-$ is the computation domain containing the base matrix, and $\Omega_2 = \Omega^-$ is the computation domain containing the inclusion. We assume that each $\Omega_i$ is partitioned by a finite element triangulation $T_{h_i}$ which can be completely independent of the other. Typically, interface-fitted nodes are generated by the partition in sub-region $\Omega_2$. When two nodes collide in sub-region $\Omega_2$, the duplicated nodes are merged to keep the procedure in the construction of meshfree approximation well-defined.

In the sub-region $\Omega_1$, the total number of meshfree nodes consists of a set of component nodes that overlap and cover the domain $\Omega$. FIG. 4-3 shows the overlapping nodes 430 of domain 420 and associated finite element mesh 435 in the partitioning of sub-region $\Omega_1$. The overlapping nodes 430 include a set of structured nodes from sub-region $\Omega_i$ and a set of interface-fitted nodes and interior nodes from sub-region $\Omega_2$. The finite element mesh 435 also serves as the integration cells needed for meshfree domain integration in sub-region $\Omega_1$ that appears in the first term on RHS (Right Hand Side) of Eqs. (17) and (18).

Let $Z_1 = \{x_I, I=1, \ldots NP\}$ be the set of distinct nodes in $\Omega_1$. NP indicates the total number of overlapping nodes in sub-region $\Omega_1$. For each $x_I \in Z_1$, $\Psi_I(x)$ denotes the corresponding meshfree shape function. We define the meshfree interpolant of $u(x)$ by the formula $$u^I(x) = \sum_{I=1}^{NP} \Psi_I(x) u(x_I) = \sum_{I=1}^{NP} \Psi_I(x) u_I \quad (20)$$

$$\forall x \in \Omega_1$$

where $u_I = u(x_I)$ is called the 'generalized' displacement of node I. In other words, $u^I(x)$ is considered as an interpolant of $u(x)$ in a generalized sense. In general, conventional meshfree approximations are not interpolants, i.e, $u_I \neq u^I(x_I)$. For this reason, special treatment is required to impose the essential boundary conditions on the global boundary $\partial\Omega$ of the model problem. We employ the generalized meshfree approximation method (GMF) to obtain the meshfree convex approximation. The first-order convex GMF approximation is constructed using the inverse tangent basis function and the cubic spline window function is chosen to be the weight function in GMF method. Giving a convex hull $co(Z_I)$ of a node set $Z_I = \{x_I, I=1, \ldots NP\} \subset R^2$ defined by $$co(Z_I) = \left\{ \sum_{I=1}^{NP} \alpha_I x_I \,\middle|\, \alpha_I \in R, \sum_{I=1}^{NP} \alpha_I = 1, \alpha_I \geq 0, x_I \in Z_1 1 \leq I \leq NP \right\} \quad (21)$$

the GMF method is to construct a convex approximation of a given (smooth) function u in the form of Eq. (20) such that the shape function $\Psi_I: co(Z_I) \rightarrow R$ satisfies the following linear polynomial reproduction property $$\sum_{I=1}^{NP} \Psi_I(x) x_I = x \forall x \in co(Z_I) \quad (22)$$

The convex approximation space constructed by GMF method is a subspace of $H_0^1(\Omega)$ and conforms to the boundary conditions if the approximating domain is convex. Ideally this conforming meshfree approximation secures $H^1$-compatibility and the homogenous Dirichlet jump condition across the interface is verified automatically. On the other hand, the meshfree approximation also introduces the non-locality across the interface. This gives rise to a solution that exhibits a smearing near the interface. To remove the smearing, we invoke a second meshfree approximation in sub-region $\Omega_2$, e.g. by zero extension in the sub-region $\Omega_1$.

To be more precise, we let $\tilde{Z}_2 = \{\tilde{x}_I, I=1, \ldots MP\} \subset Z_1$ be the subset nodes that contain the overlapping nodes in the sub-region $\Omega_2$. MP is the total number of overlapping nodes in sub-region $\Omega_2$. FIG. 4-4 shows the overlapping nodes 440 in sub-region $\Omega_2$. We also define $\tilde{\tilde{Z}}_2 = \{\tilde{\tilde{x}}_I, I=1, \ldots IP\} \subset \tilde{Z}_1 \subset Z_1$ to be the subset nodes that collect the interface-fitted nodes along the boundary of sub-region $\Omega_2$. IP is the total number of interface-fitted nodes. Also shown in FIG. 4-4 is the associated finite element mesh 445 of sub-region $\Omega_2$ as well as the integration cells for meshfree domain integration that is needed in assembly of the second term on RHS of Eqs. (17) and (18).

Analogously, every function $\tilde{u}_h(x) \in \tilde{V}_{h2}(\Omega_2)$ has a unique representation of the form $$\tilde{u}_h(x) = \sum_{I=1}^{MP} \tilde{\Psi}_I(x) \tilde{u}_I \quad (23)$$

$$\forall x \in \Omega_2$$

Since the sub-region $\Omega_2$ is assumed to be convex, the subspace $\tilde{V}_{h2}(\Omega_2)$ is defined by $$\tilde{V}_{h2}(\Omega_2) = \{v : v|_{\Omega_2} \in H^1(\Omega_2), v = 0 \text{ on } \partial\Omega \cup \partial\Omega_2\} \quad (24)$$

Apparently, the subspace $\tilde{V}_{h2}(\Omega_2)$ is not a subset of subspace $V_h(\Omega_1)$, i.e., $\tilde{V}_{h2}(\Omega_2) \not\subset V_h(\Omega_1)$. Since the approximations in sub-region $\Omega_1$ and sub-region $\Omega_2$ are constructed independently, the meshfree shape functions $\tilde{\Psi}_I(x)$ and $\Psi_I(x)$ of the same node $x_I \in \tilde{Z}_2 \subset Z_1$ are not necessarily the same. This is true in particular when support of node $x_I$ covers the interface $\Gamma$, i.e., $$\tilde{\Psi}_I(x) \neq \Psi_I(x) \text{ for } x_I \in \tilde{Z}_2 \subset Z_1 \text{ and supp}(x_I) \cap \Gamma \neq 0 \quad (25)$$

The support of shape function in sub-region $\Omega_2$ is defined by $$\text{supp}(x_I) = \text{supp}(\tilde{\Psi}_I(x)) = \{x | \in \Omega_2 \text{ and } \tilde{\Psi}_I(x) \neq 0\} \quad (26)$$

As a result, it leads to a non-conforming meshfree approximation and the continuity of displacement across the interface is not ensured. A one-dimensional example is shown in FIG. 4-5 to illustrate the non-conforming meshfree approximation using the embedded meshfree method. Because the homogenous Dirichlet jump condition is not satisfied at the interface, a procedure like the mortar technique for the coupling of two different triangulations is needed to achieve an optimal approximation.

Construction of Meshfree Approximation and Modified Variational Formulation

In mortar finite element method, the non-conforming problem is caused by the non-matching meshes across the interface where no sharing nodes are established to provide the displacement continuity. Therefore an additional constraint equation corresponding to the Dirichlet jump condition is required to connect the disjointed nodes between two triangulations. In standard mortar finite element method, the constraint equation is imposed weakly across the interface and is sufficient to guarantee an approximation with a consistency error of order h if the weak solution u is smooth enough. However in embedded meshfree method, the sharing nodes are well-defined in the subset of interface-fitted nodes $\tilde{\tilde{Z}}_2 = \{\tilde{\tilde{x}}_I, I=1, \ldots IP\}$. Indeed, the non-conformity of approximation in embedded meshfree method is due to the non-matching meshfree shape functions in the overlapping domain as illustrated in FIG. 4-5. Since the sub-region $\Omega_2$ is embedded in the sub-region $\Omega_1$ ($\Omega_2 \subset \Omega_1$), we can redefine the approximation in sub-region $\Omega_1$ such that $\tilde{V}_{h2}(\Omega_2) \subset V_h(\Omega_1)$ and $\tilde{\Psi}_I(x) = \Psi_I(x)$ for $x_I \in \tilde{Z}_2 \subset Z_1$. This can be achieved by decomposing the approximation in sub-region $\Omega_1$ into two approximations in non-overlapping sub-domains ($\Omega_1 \backslash \Omega_2$ and $\Omega_2$) and enforcing the nodal-wise continuity in displacement by introducing the Kronecker-delta property to the interface-fitted nodes set $\tilde{\tilde{Z}}_2$.

Namely we define a new constrained discrete meshfree approximation space by $$\hat{V}_h(\Omega) = \prod_{i=1}^{2} \tilde{V}_{hi}(\Omega_i) \tag{27}$$

where the definition of subspace $\tilde{V}_{h2}(\Omega_2) \subset \hat{V}_h(\Omega)$ is given in Eq. (24) and additional subspace $\tilde{V}_{h1}(\Omega_1)$ is defined by $$\tilde{V}_{h1}(\Omega_1) = \{v : v|_{\Omega_1 \backslash \Omega_2} \in H^1(\Omega_1 \backslash \Omega_2), v=0 \text{ on } \partial\Omega\} \subset \hat{V}_h(\Omega) \tag{28}$$

We note that $\tilde{V}_{hi}(\Omega_i)$, i=1, 2 stand for the spaces of linear conforming meshfree approximations that satisfy homogenous Dirichlet boundary conditions on $\partial\Omega \cap \partial\Omega_i$, i=1, 2 in the sub-regions $\Omega_1 \backslash \Omega_2$ and $\Omega_2$ respectively. Let $\tilde{Z}_1 = \{\tilde{x}_l, l=1,\ldots LP\} \subset Z_1$ be the subset nodes such that $$\tilde{Z}_1 = (Z_1 \backslash \tilde{Z}_2) \cup \tilde{\tilde{Z}}_2 \text{ and } LP = NP - MP + IP \tag{29}$$

Figures 4, 5, 6:
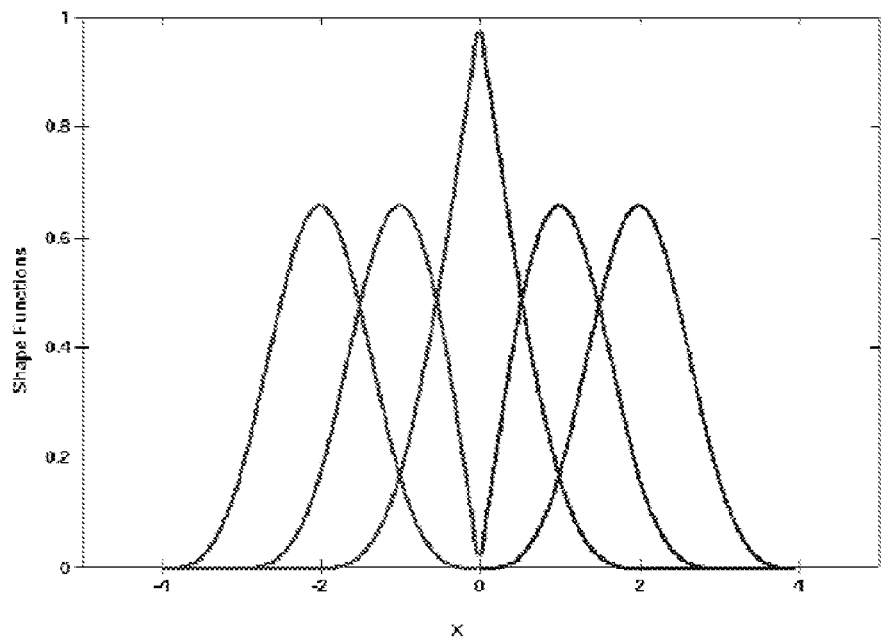
Figures 4, 5, 6, 7:
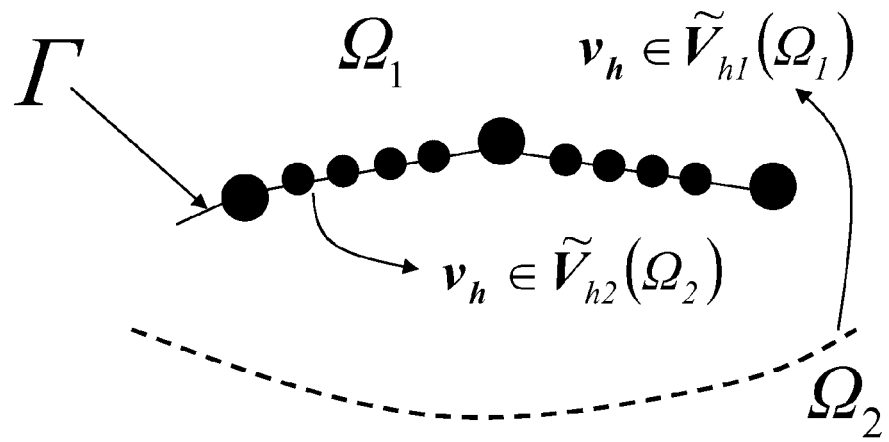
Figures 4, 5, 6, 7, 8:
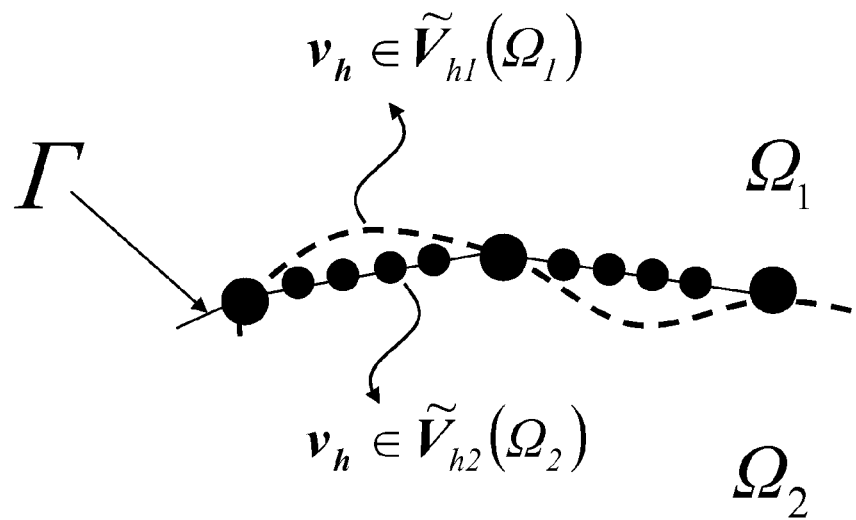
Figure 5:
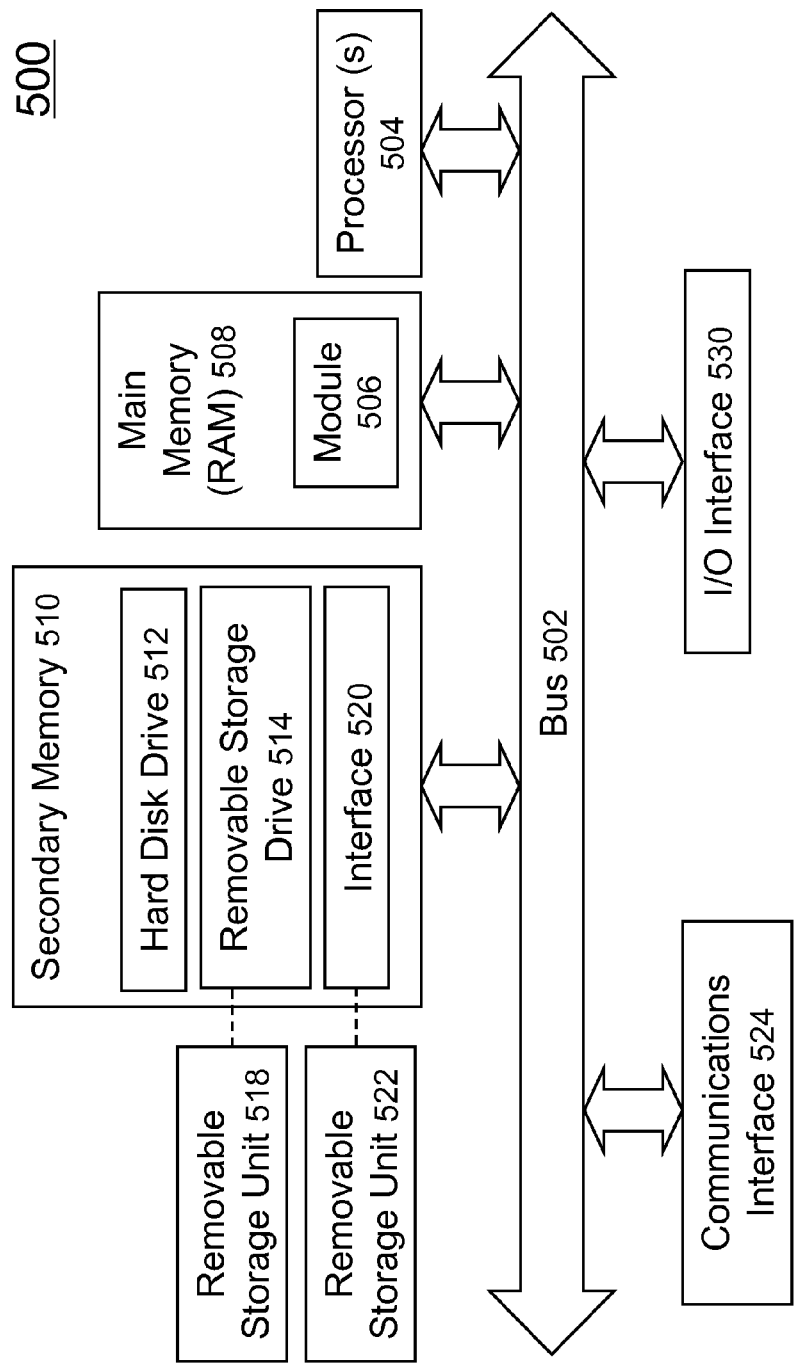

In a one dimensional case, the new approximation is conforming since $\hat{V}_h(\Omega) \subset V(\Omega)$. An improved meshfree approximation is shown in FIG. 4-6. Since the shape function of the interface-fitted node possesses the Kronecker-delta property (shown at x=0 with shape function value of 1.0), the continuity is imposed across the interface.

However, this is not the case in a two dimensional problem. Since sub-region $\Omega_1 \backslash \Omega_2$ is not convex (by assuming $\Omega_2$ is convex previously), the approximation of the interface-fitted nodes generated by the GMF method does not possess a Kronecker-delta property. In other words, the displacement continuity at the interface-fitted node does not hold. A graphic sketch of this nonconforming approximation near the interface is given in FIG. 4-7.

We impose the displacement continuity weakly and point-wisely across the interface by introducing the Kronecker-delta property to the approximation of the interface-fitted nodes. This can be done by either employing a singular kernel function to the interface-fitted nodes or applying a transformation method to those nodes whose supports cover the interface nodes. We have adopted the transformation method in this study. With the introduction of Kronecker-delta property to the shape functions at the interface-fitted nodes set $\tilde{\tilde{Z}}_2 = \{\tilde{\tilde{x}}_l, l=1, \ldots IP\}$, the reconstructed meshfree shape functions in sub-region $\Omega_1$ have the following form:

$$\Omega_1: \begin{cases} \hat{\Psi}_I^1(x) & \text{if } x_I \in \tilde{Z}_1, x \in \Omega_1 \backslash \Omega_2 \\ \hat{\Psi}_I^2(x) = \Psi_I(x) & \text{if } x_I \in \tilde{Z}_2, x \in \Omega_2 \\ \hat{\Psi}_I^1(x_J) = \hat{\Psi}_I^2(x_J) = \delta_{IJ} & \text{if } x_I, x_J \in \tilde{\tilde{Z}}_2 \end{cases} \tag{30}$$

satisfying $$u_h(x) = \begin{cases} \sum_{I=1}^{LP} \hat{\Psi}_I^1(x) u_I & \text{if } x_I \in \tilde{Z}_1, x \in \Omega_1 \backslash \Omega_2 \\ \sum_{I=1}^{MP} \hat{\Psi}_I^2(x) u_I = \sum_{I=1}^{MP} \Psi_I(x) u_I & \text{if } x_I \in \tilde{Z}_2 x \in \Omega_2 \\ \sum_{I=1}^{LP} \hat{\Psi}_I^1(x_J) u_I = \sum_{I=1}^{MP} \hat{\Psi}_I^2(x_J) u_I = u_J & \text{if } x_J \in \tilde{\tilde{Z}}_2 \end{cases} \tag{31}$$

In general $\hat{\Psi}_I^1(x) \neq \hat{\Psi}_I^2(x)$ on interface $\Gamma$ except at the interface nodes $x = x_I \in \tilde{\tilde{Z}}_2$. A nonconforming meshfree approximation with point-wise continuity across the interface is illustrated in FIG. 4-8 for a two dimensional case.

Since the displacement continuity across the interface is only imposed point-wisely at the interface-fitted nodes, the weak form of Eq. (14) is reformulated based on the nonconforming meshfree approximation. We now define the embedded meshfree solution of the elasticity interface problem as a function $u_h \in \hat{V}_h$ satisfying $$\hat{a}(u_h, v_h) = \hat{l}(v_h), \forall v_h \in \hat{V}_h \tag{32}$$

where $$\hat{a}(u_h, v_h) = \underbrace{\int_{\Omega_1 \backslash \Omega_2} \varepsilon(u_h) \cdot C^+ \cdot \varepsilon(v_h) d\Omega + \int_{\Omega_2} \varepsilon(u_h) \cdot C^+ \cdot \varepsilon(v_h) d\Omega}_{\text{intrgrating using integration cells from base matrix}} + \tag{33}$$

$$\underbrace{\int_{\Omega_2} \varepsilon(u_h) \cdot (C^- + C^+) \cdot \varepsilon(v_h) d\Omega}_{\text{integrating using integration cells from inclusion}}$$

$$\hat{l}(v_h) = \underbrace{\int_{\Omega_1 \backslash \Omega_2} f^+ \cdot v_h d\Omega + \int_{\Omega_2} f^+ \cdot v_h d\Omega}_{\text{integrating using integration cells from base matrix}} + \tag{34}$$

$$\underbrace{\int_{\Omega_2} (f^- - f^+) \cdot v_h d\Omega}_{\text{integrating using integration cells from inclusion}}$$

and the associated discrete (broken) energy norm is defined by $$\|v_h\|_{1,h} = \hat{a}(v_h, v_h)^{1/2}, v_h \in \hat{V}_h \tag{35}$$

Using the Cauchy-Schwarz inequality and triangle inequality, it can be shown that the modified bilinear form $\hat{a}(\bullet, \bullet)$ is bounded on $\hat{V}_h \times \hat{V}_h$ with respect to the broken energy norm on $\Omega$.

Lemma 1

There exists a positive constant $c_b$ such that for any $u_h$, $v_h \in \hat{V}_h$, we have $$|\hat{a}(u_h, v_h)| \leq c_b \|u_h\|_{1,h} \|v_h\|_{1,h} \tag{36}$$

Proof.

$$|\hat{a}(u_h, v_h)|^2 = \left| \begin{array}{c} \int_{\Omega_1 \backslash \Omega_2} \varepsilon(u_h) \cdot C^+ \cdot \varepsilon(v_h) d\Omega + \\ \int_{\Omega_2} \varepsilon(u_h) \cdot C^+ \cdot \varepsilon(v_h) d\Omega + \\ \int_{\Omega_2} \varepsilon(u_h) \cdot (C^- - C^+) \cdot \varepsilon(v_h) d\Omega \end{array} \right|^2 \leq \tag{37}$$

$$\int_{\Omega_1 \backslash \Omega_2} |\varepsilon(u_h) \cdot C^+ \cdot \varepsilon(v_h)|^2 d\Omega + \int_{\Omega_2} |\varepsilon(u_h) \cdot C^- \cdot \varepsilon(v_h)|^2 d\Omega \leq$$

$$\gamma_{max}^{+2}(C^+) \left( \int_{\Omega_1 \backslash \Omega_2} \|\varepsilon(u_h)\|_0^2 d\Omega \right) \left( \int_{\Omega_1 \backslash \Omega_2} \|\varepsilon(v_h)\|_0^2 d\Omega \right) +$$

$$\gamma_{max}^{-2}(C^-) \left( \int_{\Omega_2} \|\varepsilon(u_h)\|_0^2 d\Omega \right) \left( \int_{\Omega_2} \|\varepsilon(v_h)\|_0^2 d\Omega \right) \leq$$

$$\max\{\gamma_{max}^{+2}, \gamma_{max}^{-2}\} |u_h|_{1,h}^2 |v_h|_{1,h}^2 \leq c_b^2 \|u_h\|_{1,h}^2 \|v_h\|_{1,h}^2 \quad \forall u_h, v_h \in \hat{V}_h$$

In inequality (Eq. (37)), we have used the discrete semi-norm on space $\hat{V}_h$ defined by standard Sobolev notation as $$|v_h|_{1,h}^2 = |v_h|_{1,\Omega_1 \backslash \Omega_2}^2 + |v_h|_{1,\Omega_2}^2 \tag{38}$$

The constants $\gamma_{max}^+$ and $\gamma_{max}^-$ in inequality (Eq. (37)) are the largest eigenvalues of $C^+$ and $C^-$ respectively.

Lemma 2

There exists a positive constant $c_c$ such that for any $v_h \in \hat{V}_h$, we have $$\hat{a}(v_h, v_h) \geq c_c \|v_h\|_{1,h}^2 \qquad (39)$$

Proof.

Observing that $\hat{a}(v_h, v_h) = 0$ implies $v_h$ is constant. Since $v_h$ vanishes on global boundary $\partial \Omega$ and satisfies continuity at the interface-fitted nodes, we have $v_h = 0$ in $\Omega$ and thus ensure the coercivity of the modified bilinear form.

Theorem 1

Let $u \in V$ be the solution of the variational problem (Eq. (7)), the discretization problem (Eq. (32)) in embedded meshfree method admits a uniqueness solution $u_h \in \hat{V}_h$.

A Degenerated Mortar Method and Energy-Norm Error Estimate

Since $\hat{a}(\bullet, \bullet)$ is coercive, we can apply the well-known second Strang's lemma for the energy-norm error estimate.

$$\|u - u_h\|_{1,h} \leq C \left\{ \inf_{v \in \hat{V}_h} \|u - v\|_{1,h} + \sup_{w_h \in \hat{V}_h \setminus \{0\}} \frac{|\hat{a}(u - u_h, w_h)|}{\|w_h\|_{1,h}} \right\} \qquad (40)$$

where the first term on the RHS of Eq. (40) is the best approximation error which can be obtained by the meshfree approximation error estimate and the second term is the consistency error which comes from the nonconforming of $\hat{V}_h$. Assume the regularity on the exact solution $u \in H^2(\Omega)$, we have the following error estimate by Céa's inequality.

$$\inf_{v \in \hat{V}_h} \|u - v\|_{1,h} \leq \|u - I_h u\|_{1,h} \leq ch|u|_{2,\Omega} \qquad (41)$$

where h is the largest nodal support radius, i.e, $h = \sup_{I \in Z_1} \{\text{diam}(r_I)\}$. Note that it is sufficient to choose the inverse tangent basis function and $C^2$ window function in GMF method to have $H^2$ meshfree shape functions. It is also noted that the material constant C is discontinuous across the interface. Therefore it is possible that the solution u of the elasticity interface problem may not be in $H^2(\Omega)$ due to the rough solution presented in the problem.

Because the interface $\Gamma$ is associated with a one dimensional triangulation, we call this one dimensional triangulation on $\Gamma$, $\Xi_h$. Each integration segment $e_i \in \Xi_h$ is a boundary edge of integration cell (finite element triangulation) $T_{h_2}$ in $\Omega_2$. For the consistency error, we use the definition of $\hat{a}(\bullet, \bullet)$ in Eq. (33) and Galerkin orthogonality together with Green's theorem to yield $$\hat{a}(u - u_h, w_h) = \hat{a}(u, w_h) - \hat{l}(w_h) = \qquad (42)$$

$$\int_{\Omega_1 \setminus \Omega_2} \nabla \cdot (C^+ \cdot \nabla_s u) \cdot w_h d\Omega + \int_{\Omega_2} \nabla \cdot (C^- \cdot \nabla_s u) \cdot w_h d\Omega -$$

$$\int_{\Omega} f \cdot w_h d\Omega = \int_{\Omega_1 \setminus \Omega_2} \nabla \cdot (C^+ \cdot \nabla_s u) \cdot w_h d\Omega -$$

$$\left( \int_{\Omega_1 \setminus \Omega_2} \nabla \cdot (C^+ \cdot \nabla_s u) \cdot w_h d\Omega + \int_{\Omega_2} \nabla \cdot (C^- \cdot \nabla_s u) \cdot w_h d\Omega - \right.$$

$$\left. \int_{\Gamma} C \cdot \varepsilon(u) \cdot n \cdot w_h d\Gamma \right) = \sum_{e_i \in \Xi_h} \int_{e_i} (C \cdot \varepsilon(u) \cdot n) \cdot [\![w_h]\!] ds$$

where the term $$\int_{e_i} (C \cdot \varepsilon(u) \cdot n) \cdot [\![w_h]\!] ds$$

can be realized as the weak constraint equation appearing in the Lagrange multiplier-type mortar method in which $\lambda_h = C \cdot \varepsilon(u) \cdot n \in (L^2(\gamma))^2$ are Lagrange multipliers. The symbol $[\![w]\!]$ denotes the restriction of jump as defined in Eq. (2) for $w \in \Gamma$. A natural choice for the construction of Lagrange multiplier spaces in nonconforming formulation of the mortar method is to define the Lagrange multiplier basis function locally associated with the discrete nodes. From this point of view, we regard the proposed embedded meshfree method as a degenerated Lagrange multiplier-type mortar method due to the fact that the displacement jump vanishes at the interface-fitted nodes, i.e., $$[\![w_h]\!]_I = (w_I^+ - w_I^-) = 0 \; \forall I \in \tilde{Z}_2 \qquad (43)$$

Applying the point collocation method to the assembly of discrete constraint equation in mortar method and using Eq. (42) lead to the primal problem presented in Eq. (32).

$$\hat{a}(u, w_h) - \hat{l}(w_h) = \sum_{e_i \in \Xi_h} \int_{e_i} C : \varepsilon(u) \cdot n \cdot [\![w_h]\!] ds \qquad (44)$$

$$= \sum_{e_i \subset \Xi_h} \sum_{l=1}^{2} C \cdot \varepsilon(u^l) \cdot n_l \cdot (w_l^+ - w_l^-)$$

$$= 0 \; \forall \; w_h \in \hat{V}_h$$

Despite the vanishing constraint equation in the primal problem, the proposed embedded meshfree method still presents certain boundary quadrature error by different quadrature rules and requires a consistency error estimate to ensure a stable and convergent meshfree discretization. This consistency error estimate resembles the consistency error estimate of meshfree solution in standard Galerkin meshfree method using moving least-squares approximation or reproducing kernel approximation when Dirichlet boundary conditions are imposed point-wisely.

Lemma 3

Assume that $u \in H^2(\Omega)$ be the solution of elasticity interface problem in Eq. (7), there exists a constant $c_c$ independent of h and function u such that $$|\hat{a}(u, w_h) - \hat{l}(w_h)| \leq c_c h |u|_2 \|w_h\|_{1,h} \; \forall w_h \in \hat{V}_h \qquad (45)$$

Proof.

Let $D_{n^\pm}$ denotes the normal derivative in the sense of trace at the interface $\Gamma$ with the label "$\pm$" represents the limit of quantities at each side of the interface and is defined by $$D_{n^\pm} u^\pm = \sum_{i,j}^{2} C_{ij}^\pm \frac{\partial u^\pm}{\partial x_j} n_i \qquad (46)$$

where $u = u^+ = u^-$, $C = (C_{ij})_{2 \times 2}$ is the material coefficient matrix and n is the outward unit normal vector on $\Gamma$ as defined in FIG. 4-1. According to the homogenous Neumann jump condition, we have $D_n u = D_{n^+} u^+ = D_{n^-} u^-$ on material interface $\Gamma$. Using Eqs. (42), (46) and Cauchy-Schwarzs inequality followed by standard trace inequality, we have $$|\hat{a}(u, w_h) - \hat{l}(w_h)| = \left| \sum_{e_i \in \Xi_h} \int_{e_i} (C \cdot \varepsilon(u) \cdot n) \cdot [\![w_h]\!] ds \right| \leq \qquad (47)$$

$$\sum_{e \in \Xi_h} \left( \int_e |D_n u| |[\![w_h]\!]| ds \right) \leq \sum_{e_i \in \Xi_h} \left( \int_{e_i} |D_n u| ds \right) \left( \int_e |w_h^+ - w_h^-| ds \right) \leq$$

-continued $$\sum_{e_i \in \Xi_h} \left( \int_{J_{e_i}} |D_n u| \, ds \right) \left( \int_{e_i} |w_h^+| \, ds + \int_{e_i} |w_h^-| \, ds \right) \leq \sum_{e_i \in \Xi_h} |e_i|^{1/2}$$

$$\left( \int_{J_{e_i}} |D_n u|^2 \, ds \right)^{1/2} |e_i|^{1/2} \left\{ \left( \int_{e_i} |w_h^+|^2 \, ds \right)^{1/2} + \left( \int_{e_i} |w_h^-|^2 \, ds \right)^{1/2} \right\} \leq$$

$$c_{c1} h \|D_n u\|_{0,\Gamma} (\|w_h^+\|_{0,\Gamma} + \|w_h^-\|_{0,\Gamma}) \leq$$

$$c_{c1} h \|D_n u\|_1 (\|w_h\|_{1,\Omega_1/\Omega_2} + \|w_h\|_{1,\Omega_2}) \leq c_c h |u|_2 \|w_h\|_{1,h}$$

where we have related the largest nodal support radius h to the maximum length of element edge $e_i$ along the interface $\Gamma$ by defining $$\exists c_1 \geq 1, h = \sup_{I \in Z_I} h_I = \sup_{I \in Z_I} (\text{diam } r_I) = c_1 \sup_{e_j \in \Gamma} |e_j| \quad (48)$$

Lemma 3 implies $$\sup_{w_h \in \hat{V}_h \setminus \{0\}} \frac{|\hat{a}(u, w_h) - \hat{l}(w_h)|}{\|w_h\|_{1,h}} \leq c_c h |u|_2 \quad (49)$$

which indicates that the estimate of consistency error for the embedded meshfree method is of O(h). Combining inequalities (Eqs. (40), (41) and (49)), we obtain the following result for the energy error.

Proposition 1.

Let $u \in H^2(\Omega)$ and $u_h \in \hat{V}_h$ be respectively the solutions of the weak problem (7) and of the discretized problem (32). Then it holds $$\|u - u_h\|_{1,h} \leq h |u|_2 \quad (50)$$

By Proposition 1, we expect the optimal rate of convergence for embedded meshfree method to be one for u in $H^2(\Omega)$.

According to one aspect, the present invention is directed towards one or more computer systems capable of carrying out the functionality described herein. An example of a computer system 500 is shown in FIG. 5. The computer system 500 includes one or more processors, such as processor 504. The processor 504 is connected to a computer system internal communication bus 502. Various software embodiments are described in terms of this exemplary computer system. After reading this description, it will become apparent to a person skilled in the relevant art(s) how to implement the invention using other computer systems and/or computer architectures.

Computer system 500 also includes a main memory 508, preferably random access memory (RAM), and may also include a secondary memory 510. The secondary memory 510 may include, for example, one or more hard disk drives 512 and/or one or more removable storage drives 514, representing a floppy disk drive, a magnetic tape drive, an optical disk drive, etc. The removable storage drive 514 reads from and/or writes to a removable storage unit 518 in a well-known manner. Removable storage unit 518, represents a floppy disk, magnetic tape, optical disk, etc. which is read by and written to by removable storage drive 514. As will be appreciated, the removable storage unit 518 includes a computer usable storage medium having stored therein computer software and/or data.

In alternative embodiments, secondary memory 510 may include other similar means for allowing computer programs or other instructions to be loaded into computer system 500. Such means may include, for example, a removable storage unit 522 and an interface 520. Examples of such may include a program cartridge and cartridge interface (such as that found in video game devices), a removable memory chip (such as an Erasable Programmable Read-Only Memory (EPROM), Universal Serial Bus (USB) flash memory, or PROM) and associated socket, and other removable storage units 522 and interfaces 520 which allow software and data to be transferred from the removable storage unit 522 to computer system 500. In general, Computer system 500 is controlled and coordinated by operating system (OS) software, which performs tasks such as process scheduling, memory management, networking and I/O services.

There may also be a communications interface 524 connecting to the bus 502. Communications interface 524 allows software and data to be transferred between computer system 500 and external devices. Examples of communications interface 524 may include a modem, a network interface (such as an Ethernet card), a communications port, a Personal Computer Memory Card International Association (PCMCIA) slot and card, etc. Software and data transferred via communications interface 524 are in the form of signals which may be electronic, electromagnetic, optical, or other signals capable of being received by communications interface 524. The computer 500 communicates with other computing devices over a data network based on a special set of rules (i.e., a protocol). One of the common protocols is TCP/IP (Transmission Control Protocol/Internet Protocol) commonly used in the Internet. In general, the communication interface 524 manages the assembling of a data file into smaller packets that are transmitted over the data network or reassembles received packets into the original data file. In addition, the communication interface 524 handles the address part of each packet so that it gets to the right destination or intercepts packets destined for the computer 500. In this document, the terms "computer program medium", "computer usable medium", and "computer readable medium" are used to generally refer to media such as removable storage drive 514, and/or a hard disk installed in hard disk drive 512. These computer program products are means for providing software to computer system 500. The invention is directed to such computer program products.

The computer system 500 may also include an input/output (I/O) interface 530, which provides the computer system 500 to access monitor, keyboard, mouse, printer, scanner, plotter, and alike.

Computer programs (also called computer control logic) are stored as application modules 506 in main memory 508 and/or secondary memory 510. Computer programs may also be received via communications interface 524. Such computer programs, when executed, enable the computer system 500 to perform the features of the present invention as discussed herein. In particular, the computer programs, when executed, enable the processor 504 to perform features of the present invention. Accordingly, such computer programs represent controllers of the computer system 500.

In an embodiment where the invention is implemented using software, the software may be stored in a computer program product and loaded into computer system 500 using removable storage drive 514, hard drive 512, or communications interface 524. The application module 506, when executed by the processor 504, causes the processor 504 to perform the functions of the invention as described herein.

The main memory 508 may be loaded with one or more application modules 506 that can be executed by one or more processors 504 with or without a user input through the I/O interface 530 to achieve desired tasks. In operation, when at least one processor 504 executes one of the application modules 506, the results are computed and stored in the secondary memory 510 (i.e., hard disk drive 512). The status of the computer simulation of embedded bi-material (e.g., meshfree method results) is reported to the user via the I/O interface 530 either in a text or in a graphical representation.

Although the present invention has been described with reference to specific embodiments thereof, these embodiments are merely illustrative, and not restrictive of, the present invention. Various modifications or changes to the specifically disclosed exemplary embodiments will be suggested to persons skilled in the art. For example, whereas only one immersed material has been shown and described, other numbers of immersed materials may be employed, for example, two, three or four immersed materials within a base material. Additionally, the shape of base material has been shown and described as a rectangular and the immersed material as a circular shape, the present invention sets no limit to the shapes (i.e., any enclosed shapes can be used for either material). Furthermore, only two-dimensional examples have been shown and described, the present invention applies to three-dimensional problem. In summary, the scope of the invention should not be restricted to the specific exemplary embodiments disclosed herein, and all modifications that are readily suggested to those of ordinary skill in the art should be included within the spirit and purview of this application and scope of the appended claims

What is claimed is:

1. A method of numerically simulating structural behaviors of an embedded bi-material, said method comprising:
    receiving, in a computer system having one or more application modules configured for simulating structural behaviors of an embedded bi-material installed thereon, a configuration of an embedded bi-material that contains a base material and at least one immersed material;
    independently creating first and second computerized grid models from the received configuration by said one or more application modules, said first computerized grid model representing the embedded bi-material in its entirety and said second computerized grid model representing the immersed material;
    deriving a set of interface nodes from said second computerized grid model by said one or more application modules, said set of interface nodes defining a material interface between the base material and the immersed material;
    creating a first group of meshfree nodes representing the embedded bi-material by said one or more application modules, said first group of meshfree nodes being derived from said first and said second computerized grid models;
    designating those of the first group of meshfree nodes located within a space bordered by the material interface as a second group of meshfree nodes by said one or more application modules; and
    obtaining simulated structural behaviors of the embedded bi-material by said one or more application modules using said first and said second groups of meshfree nodes with a meshfree method that combines results of at least first and second meshfree approximations, said first meshfree approximation covering said first group of meshfree nodes and basing upon said base material's properties while said second meshfree approximation covering the second group of meshfree nodes and basing upon a property differential between said immersed material and said base material.

2. The method of claim 1, wherein the immersed material is entirely embedded in the base material.

3. The method of claim 1, wherein said first computerized grid model and said second computerized grid model share no correlation.

4. The method of claim 1, wherein said set of interface nodes are outer border or edge nodes of the said second computerized grid model.

5. The method of claim 1, wherein said creating the first group of meshfree nodes representing the embedded bi-material further comprises:
    combining respective nodes from said first and said second computerized grid models; and
    removing an existed node when a newly added node is a duplicate of the existed node during said combining respective nodes.

6. The method of claim 1, wherein said first and said second meshfree approximation are achieved by performing mathematical integration of said first and said second groups of meshfree nodes over respective nodal support.

7. The method of claim 6, wherein said first and said second meshfree approximations further include providing Kronecker-delta property at the set of interface nodes.

8. A non-transitory computer readable medium containing computer executable instructions for numerically simulating structural behaviors of an embedded bi-material by a method comprising:
    receiving a configuration of an embedded bi-material that contains a base material and at least one immersed material;
    independently creating first and second computerized grid models from the received configuration, said first computerized grid model representing the embedded bi-material in its entirety and said second computerized grid model representing the immersed material;
    deriving a set of interface nodes from said second computerized grid model, said set of interface nodes defining a material interface between the base material and the immersed material;
    creating a first group of meshfree nodes representing the embedded bi-material, said first group of meshfree nodes being derived from said first and said second computerized grid models;
    designating those of the first group of meshfree nodes located within a space bordered by the material interface as a second group of meshfree nodes; and
    obtaining simulated structural behaviors of the embedded bi-material using said first and said second groups of meshfree nodes with a meshfree method that combines results of at least first and second meshfree approximations, said first meshfree approximation covering said first group of meshfree nodes and basing upon said base material's properties while said second meshfree approximation covering the second group of meshfree nodes and basing upon a property differential between said immersed material and said base material.

9. The non-transitory computer readable medium of claim 8, wherein the immersed material is entirely embedded in the base material.

10. The non-transitory computer readable medium of claim 8, wherein said first computerized grid model and said second computerized grid model share no correlation.

11. The non-transitory computer readable medium of claim 8, wherein said set of interface nodes are outer border or edge nodes of the said second computerized grid model.

12. The non-transitory computer readable medium of claim 8, wherein said creating the first group of meshfree nodes representing the embedded bi-material further comprises:

combining respective nodes from said first and said second computerized grid models; and removing an existed node when a newly added node is a duplicate of the existed node during said combining respective nodes.

13. The non-transitory computer readable medium of claim 8, wherein said first and said second meshfree approximation are achieved by performing mathematical integration of said first and said second groups of meshfree nodes over respective nodal support.

14. The non-transitory computer readable medium of claim 13, wherein said first and said second meshfree approximations further include providing Kronecker-delta property at the set of interface nodes.

15. A system for numerically simulating structural behaviors of an embedded bi-material, the system comprising:

an input/output (I/O) interface;

a memory for storing computer readable code for one or more application modules configured for simulating structural behaviors of an embedded bi-material;

at least one processor coupled to the memory, said at least one processor executing the computer readable code in the memory to cause said one or more application modules to perform operations of:

receiving a configuration of an embedded bi-material that contains a base material and at least one immersed material;

independently creating first and second computerized grid models from the received configuration, said first computerized grid model representing the embedded bi-material in its entirety and said second computerized grid model representing the immersed material;

deriving a set of interface nodes from said second computerized grid model, said set of interface nodes defining a material interface between the base material and the immersed material;

creating a first group of meshfree nodes representing the embedded bi-material, said first group of meshfree nodes being derived from said first and said second computerized grid models;

designating those of the first group of meshfree nodes located within a space bordered by the material interface as a second group of meshfree nodes; and obtaining simulated structural behaviors of the embedded bi-material using said first and said second groups of meshfree nodes with a meshfree method that combines results of at least first and second meshfree approximations, said first meshfree approximation covering said first group of meshfree nodes and basing upon said base material's properties while said second meshfree approximation covering the second group of meshfree nodes and basing upon a property differential between said immersed material and said base material.

16. The system of claim 15, wherein the immersed material is entirely embedded in the base material.

17. The system of claim 15, wherein said set of interface nodes are outer border or edge nodes of the said second computerized grid model.

18. The system of claim 15, wherein said creating the first group of meshfree nodes representing the embedded bi-material further comprises:

combining respective nodes from said first and said second computerized grid models; and removing an existed node when a newly added node is a duplicate of the existed node during said combining respective nodes.

19. The system of claim 15, wherein said first and said second meshfree approximation are achieved by performing mathematical integration of said first and said second groups of meshfree nodes over respective nodal support.

20. The method of claim 19, wherein said first and said second meshfree approximations further include providing Kronecker-delta property at the set of interface nodes.

* * * * *